United States Patent [19]

Hartl et al.

[11] Patent Number: 4,806,348

[45] Date of Patent: Feb. 21, 1989

[54] METHOD FOR INDUCING ANTIBODY FORMATION

[75] Inventors: Roland Hartl, Muenster-Altheim; Dieter Kraemer, Mainz, both of Fed. Rep. of Germany

[73] Assignee: Röhm GmbH, Darmstadt, Fed. Rep. of Germany

[21] Appl. No.: 65,326

[22] Filed: Jun. 22, 1987

[30] Foreign Application Priority Data

Jun. 28, 1986 [DE] Fed. Rep. of Germany ....... 3621719

[51] Int. Cl.$^4$ ..................... A61K 39/00; A61K 45/02; A61K 39/42; A61K 39/40
[52] U.S. Cl. ......................... 424/85; 424/86; 424/87; 530/387
[58] Field of Search ............................. 424/85, 86, 87; 530/387

[56] References Cited

U.S. PATENT DOCUMENTS

| | | | |
|---|---|---|---|
| 3,651,213 | 3/1972 | Wallis et al. | 424/89 |
| 3,743,720 | 7/1973 | Fosker et al. | 424/88 |
| 4,039,413 | 8/1977 | Kraemer et al. | 522/13 |
| 4,190,713 | 2/1980 | Kraemer et al. | 521/149 |
| 4,208,309 | 6/1980 | Kraemer et al. | 521/53 |
| 4,469,796 | 9/1984 | Axén et al. | 436/518 |
| 4,550,019 | 10/1985 | Polson | 424/86 |

FOREIGN PATENT DOCUMENTS

| | | |
|---|---|---|
| 0054249 | 6/1982 | European Pat. Off. . |
| 0065069 | 11/1987 | European Pat. Off. . |
| 1942196 | 9/1970 | Fed. Rep. of Germany . |
| 2430128 | 1/1976 | Fed. Rep. of Germany . |

*Primary Examiner*—John Kight
*Assistant Examiner*—C. Azpury
*Attorney, Agent, or Firm*—Curtis, Morris & Safford

[57] ABSTRACT

Antigenic substances having amino and/or carboxyl groups are bound covalently, with preservation of their electrochemical state, that is with preservation of the amino and/or carboxyl groups, to a particulate carrier which is not decomposable in the body of a vertebrate; such substances are introduced as an antigen into the body of a vertegrate to provoke an immune response of high specificity and long duration.

9 Claims, No Drawings

METHOD FOR INDUCING ANTIBODY FORMATION

The present invention relates to a method for inducing antibody formation in a vertebrate. More in particular the invention relates to such a method employing a particulate antigen formed by immobilizing an antigenic substance on a carrier with preservation of its electrochemical state.

Antibodies are widely used for diagnostic and therapeutic purposes in human and veterinary medicine as well as for analytical purposes in biochemistry. Sera for the therapy and prophylaxis of viral diseases are classical antibody preparations which have been used for many decades.

The usual method for producing antibodies consists in the administration of an antigen to the living body of a vertebrate, which then produces antibodies as a so-called immune response. These antibodies can either be isolated directly from the blood of the vertebrate, or antibody-producing cells are taken from the body being treated and developed further into antibody-producing cell cultures.

Since the antigens usually decompose rapidly in the body of the vertebrate, the antigen generally has to be administered repeatedly until there is sufficient antibody formation.

Antigens have already been bound to particulate carrier substances which themselves do not decompose in the body of the vertebrate. In many cases, such carrier-bound antigens are capable of evoking an enhanced or prolonged immune response.

The antigen may be bound to the carrier by absorption. For example, viruses, Fab fragments and pollen antigens have been bound absorptively to aluminum hydroxide gels, microcrystalline cellulose, and synthetic polymers based on acrylamide, methyl methacrylate or ionic vinyl monomers. (See U.S. Pat. No. 3,651,213; G. T. Stevenson, Nature 1974, 247 [5441], pp. 477–478; published German Patent Applications DOS No. 19 42 196 and 19 42 161). Absorptive binding has the advantage that the antigen is not altered by the binding process, and the disadvantage that the binding is reversible, so that the antigen is irretrievably lost, though more slowly than in the unbound state.

U. Groeschel-Stewart et al. covalently bound antigen proteins to polyacrylamide carriers (U. Groeschel-Stewart et al., Histochemistry 50, 271-279 [1977]) and elicited an immune response in a living rabbit body with them. Covalent binding involves amino groups of the antigen with formation of amide groups. In contrast to the original amino group, the amide group is electrically neutral. Thus the electrochemical state of the antigen is altered by this binding by way of amide groups. As a consequence, the immune response is also altered and is less specific for the unbound antigen. Moreover, the amide binding is not resistant to hydrolysis.

The object of the present invention is to bring about the formation of antibodies of increased specificity as an antigen is introduced into a living vertebrate and, in addition, to prolong the duration of antibody formation as much as possible.

In accordance with the invention, this object is accomplished through the process defined in the claims. The invention utilizes binding methods, known per se, in which the carboxyl and amino groups of the antigenic substance are not involved in the binding process in such a way that their electrochemical state would be altered. The electrochemical state is due to the fact that, depending on the pH value or on their interaction with charged particles, carboxyl and amino groups have the ability to become electrically charged ions, in other words carboxylate or ammonium ions, respectively. They retain this ability in the binding in accordance with the present invention.

As a consequence of the unaltered electrochemical state of the bound antigenic substance, an immune response is provoked in the living vertebrate body which has a higher specificity toward the uncombined antigenic substance than if the immune response had been brought about by means of an antigenic substance the binding of which had been attended by a change in its electrochemical state.

There are different ways of covalently binding antigenic substances containing amino and/or carboxyl groups to a particulate carrier material that will not decompose in the vertebrate body. The use of a carrier material having a particular composition is of decisive importance.

Synthetic polymeric carrier materials which contain oxirane groups are preferred. The oxirane groups are able to react covalently under mild conditions with primary or secondary amino groups to yield a beta-hydroxyethyl group, which attaches to the amino group as an additional substituent. Primary amino groups are transformed into secondary amino groups and secondary amino groups into tertiary amino groups. The electrochemical state remains practically unchanged.

Polymeric carriers having oxirane groups suitable for bonding biological substances for use in the present invention are taught in U.S. 4,190,713 to Kraemer et al., incorporated herein by reference. Larger particles having diameters from 5 to 1000 microns are prepared, which are copolymers comprising acrylamide, methacrylamide, methylene-bis-acrylamide and/or methylene-bis-methacrylamide and a further free radically copolymerizable unsaturated comonomer having anoxirane group therein.

U.S. Pat. No. 4,039,413 to Kraemer et al., also incorporated herein by reference, teaches methods for binding biological materials to a carrier polymer which are particularly suitable for binding antigenic substances having a peptide structure. Units of glycine, cysteine, cystine, methionine, and tryptophan are capable of being bound. The binding reaction proceeds by a free radical mechanism between a hydrocarbon group of the peptide and a group of the carrier polymer that is capable of free radical activation, with the amino and carboxyl groups remaining unchanged. Examples of groups capable of free radical activation in this sense are alkenyl and alkylphenyl groups, and preferably allyl and toluyl groups. Activation takes place in the presence of a photosensitizer by using ultraviolet light or, when also an organic peroxide is present, by means of visible light in the absence of oxygen.

Further indicative of the state of the art teaching polymer carriers having glycidyl groups and suitable for use in the present invention are the polymer particles taught in European Patent Publication No. 54,249 (=Canadian 1,117,751) having an average diameter of from 0.03 to 10 microns which are formed of a cross-linked polymer of glycidyl acrylate or methacrylate or of a copolymer thereof with hydrophilic comonomers to which immunogenic substances such as antigens or antibodies are covalently bound. The use of such immunogenic particles to bring about antibody formation in the body of a vertebrate has not been reported.

The binding of peptides or other biogenic substances having antigenic activity to carriers in latex form is also described in published European Patent Application No. 65,069. When methods there described are used for the purposes of the present invention, groups with binding activity should be selected which will from a covalent bond while leaving the amino and carboxyl groups of the antigenic substances intact. Activated carboxylic or sulfonic acid groups which would react with amino groups with formation of amides therefore are not sitable for use. In addition to the oxirane groups mentioned earlier, haloalkyl and haloalkoyl groups, for example, are suitable for binding.

An essential property of the carrier particles is their resistance to decomposition in the body of vertebrates. Carriers which are nondecomposable within the meaning of the invention are those which perform their carrier function for at least as long as the substance bound to them retains its antigenicity. Synthetic vinyl polymers in particular possess this property since they have a continuous carbon chain that cannot be cleaved by the hydrolytic enzymes which are widely dispersed in the body.

Suitable carrier polymers are described in detail in the patent publications cited above. Characteristic constituents of these polymers are:

(1) Monomers with groups having binding activity, such as:

(a) Monomers containing oxirane groups which react with amino groups of the antigenic substance with opening of the oxirane ring and alkylation of the nitrogen atom. Examples are glycidyl acrylate and methacrylate and alkylglycidyl ethers.

(b) Monomers containing haloalkyl groups, in particular chloroalkyl and bromoalkyl compounds, which react with amino groups with alkylation of the nitrogen atom. Examples are chloroacetoxyalkyl acrylates and methacrylates, bromoalkyl acrylates and methacrylates and chloroacetic vinyl esters.

(c) Monomers containing aromatic groups, which under the action of activating radiation react with a hydrocarbon group of the antigenic substance with formation of a covalent carbon-to-carbon bond. These include styrene, vinyltoluene and benzyl acrylate and methacrylate.

(d) Monomers containing alkenyl side groups, in addition to a vinyl or vinylidene group capable of free-radical polymerization, which when activated by activating radiation or by chemically generated free radicals are capable of reacting with a hydrocarbon group of the antigenic substance with formation of a covalent carbon-to-carbon bond. Examples of suitable monomers are allyl acrylate and methacrylate and polyalkyl esters of polybasic acids such as trialkyl cyanurate.

(2) Crosslinking monomers having two or more carbon-to-carbon double bonds capable of free radical polymerization in the molecule. Some of the monomers mentioned in (1)(d) have crosslinking activity in polymerization. In contrast to the monomers with alkenyl groups there mentioned, crosslinking monomers contain at least two carbon-to-carbon double bonds which are activated by vicinal electron attracting groups. Examples are the diacrylates or dimethacrylates of glycols such as ethylene glycol, propylene glycol or butylene glycol; tri- and tetraacrylates of tri- or tetra-hydric alcohols such as trimethylolpropne or pentaerythritol; methylenebisacrylamide or methacrylamide, and divinylbenzene.

(3) Hydrophilic monomers, which have a certain degree of water solubility. They preferably give at least 10 percent aqueous solutions at 25° C. Illustrative of these are acrylamide, methacrylate, vinylpyrrolidone, and hydroxyalkyl esters of acrylic or methacrylic acid, preferably with from 2 to 4 carbon atoms in the hydroxyalkyl group. These monomers are preferred because they are electrically neutral and will not affect the electrochemical state of the bound antigenic substance. In many cases, ionizable monomers can also be used. These include ethylenically unsaturated polymerizable mono- and di-carboxylic acids and their water soluble salts, for example, acrylic, methacrylic, itaconic, maleic, and fumaric acid. Also included in this group are the amino alkyl esters and aminoalkylamides of unsaturated carboxylic acids, such as the dialkylaminoalkyl esters of dialkylamino-alkylamides of acrylic and methacrylic acid, which preferably have from 1 to 5 carbon atoms in the alkyl groups. High amounts of hydrophilic monomers render the polymer water soluble, which makes it unsuitable for use as a particulate antigen. Sufficient amounts of crosslinking monomers are therefore used concurrently in this case to render the polymer water insoluble. Low amounts of crosslinker of under 5 weight percent, for example, usually give polymers that are capable of swelling in the manner of a gel, while high amounts of crosslinker yield macroporous particles that are not capable of swelling, or give particles with a hollow bead structure.

(4) Hydrophobic monomers which have a water solubility of less than 10 percent at 25° C. They can be used when the carrier polymer is produced in latex form, for example. In many cases they are able to promote binding of the antigenic substance through hydrophobic interaction with it. The monomers named under (1)(c) and (d) also fall into the group of hydrophobic monomers, which further includes the esters of polymerizable unsaturated mono- and di-carboxylic acids with aliphatic alcohols, which preferably contain from 1 to 12, and more particularly from 1 to 4, carbon atoms, for example, methyl, ethyl or butyl acrylate or methacrylate, as well as olefins such as ethylene or propylene, vinyl chloride, and vinyl esters of saturated aliphatic carboxylic acids having from 20 to 10 carbon atoms.

The relative amounts of the monomers involved will depend on their function, that is, on the amount required to produce the desired effect. To the extent that the patent publications cited above do not specify appropriate monomer amounts, the following ranges will serve as a guide:

(1) Monomers having binding activity: From 1 to 80, and preferably from 5 to 50, weight percent.

(2) Crosslinking monomers: From 0 to 50, and preferably from 0.01 to 30 , weight percent.

(3) Hydrophilic monomers: From 0 to 99, and preferably from 20 to 95, weight percent.

(4) Hydrophobic monomers: From 0 to 50, and preferably from 0 to 30, weight percent.

For the desired action of the carrier polymers it will suffice that the outermost layer of the polymer particles, and in the case of porous or macroporous polymer particles also the pore walls, consist of the polymeric material described. Beneath this layer there may be a core of another material, for example, an inorganic supporting body or a seed latex core made of a hydrophobic polymer such as polystyrene, a polyacrylic or polymethacrylic ester, or the like.

The size of the particles of the carrier polymer will depend on the manner in which they are introduced into the body of the vertebrate. If the particulate antigen is introduced into the blood stream, then the particle size preferably ranges from 0.01 to 10 microns. If it is introduced into the tissue, the particles may also be larger, for example, up to 100 microns. Carrier particles ranging in size from 0.01 to 2 microns are advantageously produced by emulsion polymerization. Particles in the size range from 1 to 50 microns are obtainable by precipitation polymerization in a medium that is a solvent for the monomers and a nonsolvent for the polymers. Suspension or bead polymerization in a medium that dissolves neither the monomer phase nor the polymer particles results in particles of a size between 20 and 100 microns. Coarser particles or bulk polymers can be comminuted by means of impact mills, homogenizers, or the like to particles in these size ranges.

The ratio by weight of antigenic substance to carrier material may vary over a wide range. High effectiveness is generally obtained in the range from 1:10 to 1:1000.

By antigenic substances are meant all substances which are capable of bringing about an immune reaction in the body of a vertebrate. They include practically all exogenous natural or synthetic macromolecules with molecular weights of over 2,000 as well as surface structures of foreign particles, such as active or inactivated bacteria or viruses composed of such macromolecules. The invention seeks to use antigenic substances which contain one or more carboxyl and/or amino groups. While the process can be carried out in the same way with antigenic substances lacking carboxyl and amino groups, the inventive advantage stemming from the maintenance of the electrochemical state then is lost. Ammonium or carboxylate groups are on a par with the amino or carboxyl groups from which they are derived by salt formation. The amino groups may be primary, secondary, or tertiary. While the presence of at least one amino group and at least one carboxyl group is the rule, antigenic substances which carry one or more amino groups but no carboxyl group, or one or more carboxyl groups but no amino group, also come within the scope of the invention.

Antigenic substances, within the meaning of the invention, includes the haptens. These are substance which in the uncombined state are not antigens but become antigens on being bound to a carrier. In practice, it is difficult to decide whether a given substance acts as an antigen also uncombined, because in many cases an immune response is elicited only after the substance has combined with an undissolved endogenous substance. Thus there is no fixed limit on the molecular weight or the size of the antigen substance. The substance may be soluble or insoluble in water. If it is water insoluble, it must be soluble in a liquid that is suitable for covalent binding.

An outstanding group of antigenic substances are those with a protein or peptide structure which may occur alone or in combination with nonprotein or nonpeptide components. Peptides and proteins generally contain both an amino group and a carboxyl group as end groups. Other groups of practical importance are the polysaccharides and the nucleic acids. When they themselves do not carry carboxyl or amino groups, they may be combined with substances containing such groups. Illustrative of the haptens are the penicillins, the tetracyclines, and digoxin.

The vertebrates treated in accordance with the invention are preferably warm blooded animals. Suitable are, for example, bovine animals, sheep, goats, horses, pigs, dogs, cats, rabbits, rats, and mice among the mammals, and chickens, ducks, geese, turkeys and pigeons among the birds. The invention is also applicable to cold blooded animals, such as fishes and reptiles.

For its administration, the particulate antigen may be suspended in an isotonic solution and injected into the blood stream or introduced into the cutaneous or connective tissue. An immune response will generally be observed after a period of incubation of from 3 to 20 days. To provoke it, a single administration of the antigen will usually suffice. The withdrawal of blood or serum containing antibody, or of cells producing antibody for the starting of cell cultures, is done conventionally as after an immune response has been evoked with the antigen not bound to carrier particles.

A better understanding of the present invention will be had by referring to the following specific Examples, given by way of illustration.

EXAMPLE 1

A powdered carrier material which is redispersible in an aqueous medium to form particles about 1 micron in diameter is prepared as follows:

5 ml of a phosphate buffer solution (pH=7, "TITRISOL"), 0.03 g of sodium lauryl sulfate, and 0.2 g of the sodium salt of 4,4'-azobis-(4-cyanovalerianic acid) are dissolved in 100 ml of water present in a polymerization vessel equipped as described earlier. The mixture is heated to 80° C. and, over a period of three hours, an emulsion is added comprising:

0.1 g of sodium lauryl sulfate,
0.5 g of the sodium salt of 4,4'-azobis -(4-cyanovalerianic acid),
80 g of methyl methacrylate,
15 g of [2-(2,4,6-tribromophenoxy) -ethyl]-methacrylate,
5 g of ethylene glycol dimethacrylate, and
200 g of water.

Subsequently, a solution of 5 g of methacrylamide in 75 g of water and a monomer mixture comprising
10 g of glycidyl methacrylate,
1 g of ethylene glycol dimethacrylate, and
9 g of methyl methcrylate
are added simultaneously over a period of 90 minutes. The mixture is held for a further 60 minutes at 80° C.

A dispersion of low viscosity having a solids content of about 25 percent is obtained. The particle size is 0.3 micron. The content of oxirane groups is 31 percent, based on the glycidyl merthacrylate introduced (determined by titration with sodium thiosulfate).

2 g of this carrier material, in the form of a powder redispersible into particles about 1 micron in diameter, are suspended in 4 ml of a buffer solution having a pH=7.3 (1.0M sodium phosphate plus 0.15 NaCl), and 20 mg of bovine serum albumin (BSA) (manufactured by Miles Laboratories, Lot No. 63, Code No. 81-001) are added to it. The suspension is allowed to stand for 72 hours at room temperature. Then it is repeatedly washed with water and centrifuged. The Bradford protein test (run with the "Bio-Rad" test kit) shows a content of 4.4 mg of covalently bound BSA per gram of carrier material.

455 mg of the immobolizate obtained, containing 2.0 mg of BSA, are mixed with 1 ml of incomplete Freund's adjuvant (an adjuvant commonly used in immunochemistry) and suspended within 40 minutes by ultrasound to form a water-in-oil emulsion. The suspension, divided into 10 individual doses, is administered subcutaneously to a rabbit. The entire treatment is repeated after three weeks for enhancement of the immune effect. After another four weeks, 10 ml blood are taken from the ear vein of the rabbit being treated. The withdrawn blood is allowed to stand for one hour at 37° C. and for another 36 hours in a refrigerator. The antiserum is then conventionally separated from the blood clot.

The antibody concentration in the antiserum can be readily determined by means of the capillary test. To this end, the antigen, that is BSA, is dissolved to a concentration of 1 mg/ml in PBS (phosphate buffer, saline, pH 7.3). The solution is introduced into a glass capillary tube to a height of 3 cm. Approximately the same amount of the antiserum obtained from the blood of the rabbit is drawn into the capillary, held at a slant, and the lower end of the capillary is sealed with putty. The capillary tube is then allowed to stand for one hour at 37° C. and for another 48 hours at from 5° C. to 8° C., and the height of the settled precipitate at the lower end of the capillary is then measured. A precipitate height of 12 mm is measured. A precipitate height of 10 mm corresponds to an antibody concentration of about 1 mg/ml. On this basis, the antibody concentration in the antiserum is 1.2 mg/ml.

For comparison, the blood serum of an untreated rabbit is treated with the antiserum in the same manner. No precipitate forms in the capillary tube.

In a further test, the immobilized BSA alone (without incomplete Freund's adjuvant) is administered subcutaneously to a rabbit and the treatment is reported as described above. In the immune test, a precipitate height of only 4 mm is obtained, which corresponds to an antibody concentration of 0.4 mg/ml. This demonstrates the enhanced activity of the immobilized BSA in the presence of incomplete Freund's adjuvant.

When insulin or thyroid stimulating hormone (TSH) is used in place of BSA, the corresponding antisera can be produced accordingly. They can then be used diagnostically for the determination of the insulin of TSH.

We claim:

1. A method for inducing antibody formation in the living body of a vertebrate, which method comprises immobilizing a soluble antigenic substance containing amino and/or carboxyl groups by covalently binding it with oxirane groups present on a particulate carrier which is not decomposable in the vertebrate body, whereby a particulate antigen is formed wherein the amino and/or carboxyl groups of said antigenic substance are preserved, and then introducing said antigen into a vertebrate body.

2. A method as in claim 1 wherein said carrier comprises, at least in its outermost layer reacting with said antigenic substance
   (1) from 1 to 88 weight percent of a monomer having binding activity and containing an oxirane group,
   (2) from 0 to 50 weight percent of a cross-linking monomer having two or more carbon-to-carbon double bonds polymerizable by the use of free radical initiators in the molecule;
   (3) from 0 to 99 weight percent of a hydrophilic monomer which forms at least 10 percent aqueous solutions at 25° C.; and
   (4) from 0 to 50 weight percent of a hydrophobic monomer which form less than 10 percent aqueous solutions at 25° C.

3. A method as in claim 1 wherein said antigenic substance is bound to a particulate carrier having an average particle diameter of 0.01 to 100 microns.

4. A method as in claim 1 wherein said antigenic substance is a hapten containing one or more amino and/or carboxyl groups.

5. A method as in claim 4 wherein said antigenic substance is bound to a carrier in the form of an aqueous latex having a particle size of 0.01 to 2 microns.

6. A method as in claim 1 wherein said antigenic substance has a protein or peptide structure.

7. A method as in claim 1 wherein said particulate antigen is introduced into the body of a warm blooded vertebrate.

8. A method as in claim 7 wherein said particulate antigen is introduced subcutaneously into the body of the vertebrate.

9. A method as in claim 7 wherein said particulate antigen is introduced into the body of the vertebrate as a water-in-oil emulsion.

* * * * *